(12) United States Patent  (10) Patent No.: US 9,134,254 B2
Ramachandran  (45) Date of Patent: Sep. 15, 2015

(54) DETERMINING A POSITION OF INSPECTION SYSTEM OUTPUT IN DESIGN DATA SPACE

(71) Applicant: KLA-Tencor Corporation, Milpitas, CA (US)

(72) Inventor: Vijayakumar Ramachandran, Sunnyvale, CA (US)

(73) Assignee: KLA-Tencor Corp., Milpitas, CA (US)

( * ) Notice: Subject to any disclaimer, the term of this patent is extended or adjusted under 35 U.S.C. 154(b) by 281 days.

(21) Appl. No.: 13/830,539

(22) Filed: Mar. 14, 2013

(65) Prior Publication Data

US 2014/0195992 A1    Jul. 10, 2014

Related U.S. Application Data

(60) Provisional application No. 61/749,806, filed on Jan. 7, 2013.

(51) Int. Cl.
*G06F 17/50* (2006.01)
*G01N 21/95* (2006.01)

(52) U.S. Cl.
CPC .................................. *G01N 21/9501* (2013.01)

(58) Field of Classification Search
USPC ....................................................... 716/50, 51
See application file for complete search history.

(56) References Cited

U.S. PATENT DOCUMENTS

| | | |
|---|---|---|
| 3,495,269 A | 2/1970 | Mutschler et al. |
| 3,496,352 A | 2/1970 | Jugle |
| 3,909,602 A | 9/1975 | Micka |
| 4,015,203 A | 3/1977 | Verkuil |
| 4,247,203 A | 1/1981 | Levy et al. |
| 4,347,001 A | 8/1982 | Levy et al. |
| 4,378,159 A | 3/1983 | Galbraith |
| 4,448,532 A | 5/1984 | Joseph et al. |
| 4,475,122 A | 10/1984 | Green |
| 4,532,650 A | 7/1985 | Wihl et al. |
| 4,555,798 A | 11/1985 | Broadbent, Jr. et al. |
| 4,578,810 A | 3/1986 | MacFarlane et al. |

(Continued)

FOREIGN PATENT DOCUMENTS

| CN | 1339140 | 3/2002 |
|---|---|---|
| CN | 1398348 | 2/2003 |

(Continued)

OTHER PUBLICATIONS

U.S. Appl. No. 60/681,095, filed May 13, 2005 by Nehmadi et al.

(Continued)

*Primary Examiner* — Sun Lin
(74) *Attorney, Agent, or Firm* — Ann Marie Mewherter

(57) ABSTRACT

Systems and methods for determining a position of output of an inspection system in design data space are provided. One method includes merging more than one feature in design data for a wafer into a single feature that has a periphery that encompasses all of the features that are merged. The method also includes storing information for the single feature without the design data for the features that are merged. The information includes a position of the single feature in design data space. The method further includes aligning output of an inspection system for the wafer to the information for the single feature such that positions of the output in the design data space can be determined based on the position of the single feature in the design data space.

34 Claims, 2 Drawing Sheets

(56) References Cited

U.S. PATENT DOCUMENTS

| | | |
|---|---|---|
| 4,579,455 A | 4/1986 | Levy et al. |
| 4,595,289 A | 6/1986 | Feldman et al. |
| 4,599,558 A | 7/1986 | Castellano, Jr. et al. |
| 4,633,504 A | 12/1986 | Wihl |
| 4,641,353 A | 2/1987 | Kobayashi |
| 4,641,967 A | 2/1987 | Pecen |
| 4,734,721 A | 3/1988 | Boyer et al. |
| 4,748,327 A | 5/1988 | Shinozaki et al. |
| 4,758,094 A | 7/1988 | Wihl et al. |
| 4,766,324 A | 8/1988 | Saadat et al. |
| 4,799,175 A | 1/1989 | Sano et al. |
| 4,805,123 A | 2/1989 | Specht et al. |
| 4,812,756 A | 3/1989 | Curtis et al. |
| 4,814,829 A | 3/1989 | Kosugi et al. |
| 4,817,123 A | 3/1989 | Sones et al. |
| 4,845,558 A | 7/1989 | Tsai et al. |
| 4,877,326 A | 10/1989 | Chadwick et al. |
| 4,926,489 A | 5/1990 | Danielson et al. |
| 4,928,313 A | 5/1990 | Leonard et al. |
| 5,046,109 A | 9/1991 | Fujimori et al. |
| 5,124,927 A | 6/1992 | Hopewell et al. |
| 5,189,481 A | 2/1993 | Jann et al. |
| 5,355,212 A | 10/1994 | Wells et al. |
| 5,444,480 A | 8/1995 | Sumita |
| 5,453,844 A | 9/1995 | George et al. |
| 5,481,624 A | 1/1996 | Kamon |
| 5,485,091 A | 1/1996 | Verkuil |
| 5,497,381 A | 3/1996 | O'Donoghue et al. |
| 5,528,153 A | 6/1996 | Taylor et al. |
| 5,544,256 A | 8/1996 | Brecher et al. |
| 5,563,702 A | 10/1996 | Emery et al. |
| 5,572,598 A | 11/1996 | Wihl et al. |
| 5,578,821 A | 11/1996 | Meisberger et al. |
| 5,594,247 A | 1/1997 | Verkuil et al. |
| 5,608,538 A | 3/1997 | Edgar et al. |
| 5,619,548 A | 4/1997 | Koppel |
| 5,621,519 A | 4/1997 | Frost et al. |
| 5,644,223 A | 7/1997 | Verkuil |
| 5,650,731 A | 7/1997 | Fung et al. |
| 5,661,408 A | 8/1997 | Kamieniecki et al. |
| 5,689,614 A | 11/1997 | Gronet et al. |
| 5,694,478 A | 12/1997 | Braier et al. |
| 5,696,835 A | 12/1997 | Hennessey et al. |
| 5,703,969 A | 12/1997 | Hennessey et al. |
| 5,716,889 A | 2/1998 | Tsuji et al. |
| 5,737,072 A | 4/1998 | Emery et al. |
| 5,742,658 A | 4/1998 | Tiffin et al. |
| 5,754,678 A | 5/1998 | Hawthorne et al. |
| 5,767,691 A | 6/1998 | Verkuil |
| 5,767,693 A | 6/1998 | Verkuil |
| 5,771,317 A | 6/1998 | Edgar |
| 5,773,989 A | 6/1998 | Edelman et al. |
| 5,774,179 A | 6/1998 | Chevrette et al. |
| 5,795,685 A | 8/1998 | Liebmann et al. |
| 5,822,218 A | 10/1998 | Moosa et al. |
| 5,831,865 A | 11/1998 | Berezin et al. |
| 5,834,941 A | 11/1998 | Verkuil |
| 5,852,232 A | 12/1998 | Samsavar et al. |
| 5,866,806 A | 2/1999 | Samsavar et al. |
| 5,874,733 A | 2/1999 | Silver et al. |
| 5,884,242 A | 3/1999 | Meier et al. |
| 5,889,593 A | 3/1999 | Bareket |
| 5,917,332 A | 6/1999 | Chen et al. |
| 5,932,377 A | 8/1999 | Ferguson et al. |
| 5,940,458 A | 8/1999 | Suk |
| 5,948,972 A | 9/1999 | Samsavar et al. |
| 5,955,661 A | 9/1999 | Samsavar et al. |
| 5,965,306 A | 10/1999 | Mansfield et al. |
| 5,978,501 A | 11/1999 | Badger et al. |
| 5,980,187 A | 11/1999 | Verhovsky |
| 5,986,263 A | 11/1999 | Hiroi et al. |
| 5,991,699 A | 11/1999 | Kulkarni et al. |
| 5,999,003 A | 12/1999 | Steffan et al. |
| 6,011,404 A | 1/2000 | Ma et al. |
| 6,014,461 A | 1/2000 | Hennessey et al. |
| 6,040,911 A | 3/2000 | Nozaki et al. |
| 6,040,912 A | 3/2000 | Zika et al. |
| 6,052,478 A | 4/2000 | Wihl et al. |
| 6,060,709 A | 5/2000 | Verkuil et al. |
| 6,072,320 A | 6/2000 | Verkuil |
| 6,076,465 A | 6/2000 | Vacca et al. |
| 6,078,738 A | 6/2000 | Garza et al. |
| 6,091,257 A | 7/2000 | Verkuil et al. |
| 6,091,846 A | 7/2000 | Lin et al. |
| 6,097,196 A | 8/2000 | Verkuil et al. |
| 6,097,887 A | 8/2000 | Hardikar et al. |
| 6,104,206 A | 8/2000 | Verkuil |
| 6,104,835 A | 8/2000 | Han |
| 6,117,598 A | 9/2000 | Imai |
| 6,121,783 A | 9/2000 | Horner et al. |
| 6,122,017 A | 9/2000 | Taubman |
| 6,122,046 A | 9/2000 | Almogy |
| 6,137,570 A | 10/2000 | Chuang et al. |
| 6,141,038 A | 10/2000 | Young et al. |
| 6,146,627 A | 11/2000 | Muller et al. |
| 6,171,737 B1 | 1/2001 | Phan et al. |
| 6,175,645 B1 | 1/2001 | Elyasaf et al. |
| 6,184,929 B1 | 2/2001 | Noda et al. |
| 6,184,976 B1 | 2/2001 | Park et al. |
| 6,191,605 B1 | 2/2001 | Miller et al. |
| 6,201,999 B1 | 3/2001 | Jevtic |
| 6,202,029 B1 | 3/2001 | Verkuil et al. |
| 6,205,239 B1 | 3/2001 | Lin et al. |
| 6,215,551 B1 | 4/2001 | Nikoonahad et al. |
| 6,224,638 B1 | 5/2001 | Jevtic et al. |
| 6,233,719 B1 | 5/2001 | Hardikar et al. |
| 6,246,787 B1 | 6/2001 | Hennessey et al. |
| 6,248,485 B1 | 6/2001 | Cuthbert |
| 6,248,486 B1 | 6/2001 | Dirksen et al. |
| 6,259,960 B1 | 7/2001 | Inokuchi |
| 6,266,437 B1 | 7/2001 | Eichel et al. |
| 6,267,005 B1 | 7/2001 | Samsavar et al. |
| 6,268,093 B1 | 7/2001 | Kenan et al. |
| 6,272,236 B1 | 8/2001 | Pierrat et al. |
| 6,282,309 B1 | 8/2001 | Emery |
| 6,292,582 B1 | 9/2001 | Lin et al. |
| 6,295,374 B1 | 9/2001 | Robinson et al. |
| 6,324,298 B1 | 11/2001 | O'Dell et al. |
| 6,344,640 B1 | 2/2002 | Rhoads |
| 6,363,166 B1 | 3/2002 | Wihl et al. |
| 6,366,687 B1 | 4/2002 | Aloni et al. |
| 6,373,975 B1 | 4/2002 | Bula et al. |
| 6,388,747 B2 | 5/2002 | Nara et al. |
| 6,393,602 B1 | 5/2002 | Atchison et al. |
| 6,407,373 B1 | 6/2002 | Dotan |
| 6,415,421 B2 | 7/2002 | Anderson et al. |
| 6,445,199 B1 | 9/2002 | Satya et al. |
| 6,451,690 B1 | 9/2002 | Matsumoto et al. |
| 6,459,520 B1 | 10/2002 | Takayama |
| 6,466,314 B1 | 10/2002 | Lehman |
| 6,466,315 B1 | 10/2002 | Karpol et al. |
| 6,470,489 B1 | 10/2002 | Chang et al. |
| 6,483,938 B1 | 11/2002 | Hennessey et al. |
| 6,513,151 B1 | 1/2003 | Erhardt et al. |
| 6,526,164 B1 | 2/2003 | Mansfield et al. |
| 6,529,621 B1 | 3/2003 | Glasser et al. |
| 6,535,628 B2 | 3/2003 | Smargiassi et al. |
| 6,539,106 B1 | 3/2003 | Gallarda et al. |
| 6,569,691 B1 | 5/2003 | Jastrzebski et al. |
| 6,581,193 B1 | 6/2003 | McGhee et al. |
| 6,593,748 B1 | 7/2003 | Halliyal et al. |
| 6,597,193 B2 | 7/2003 | Lagowski et al. |
| 6,602,728 B1 | 8/2003 | Liebmann et al. |
| 6,608,681 B2 | 8/2003 | Tanaka et al. |
| 6,614,520 B1 | 9/2003 | Bareket et al. |
| 6,631,511 B2 | 10/2003 | Haffner et al. |
| 6,636,301 B1 | 10/2003 | Kvamme et al. |
| 6,642,066 B1 | 11/2003 | Halliyal et al. |
| 6,658,640 B2 | 12/2003 | Weed |
| 6,665,065 B1 | 12/2003 | Phan et al. |
| 6,670,082 B2 | 12/2003 | Liu et al. |
| 6,680,621 B2 | 1/2004 | Savtchouk |
| 6,691,052 B1 | 2/2004 | Maurer |
| 6,701,004 B1 | 3/2004 | Shykind et al. |

(56) References Cited

U.S. PATENT DOCUMENTS

| | | |
|---|---|---|
| 6,718,526 B1 | 4/2004 | Eldredge et al. |
| 6,721,695 B1 | 4/2004 | Chen et al. |
| 6,734,696 B2 | 5/2004 | Horner et al. |
| 6,738,954 B1 | 5/2004 | Allen et al. |
| 6,748,103 B2 | 6/2004 | Glasser et al. |
| 6,751,519 B1 | 6/2004 | Satya et al. |
| 6,753,954 B2 | 6/2004 | Chen |
| 6,757,645 B2 | 6/2004 | Chang et al. |
| 6,759,655 B2 | 7/2004 | Nara et al. |
| 6,771,806 B1 | 8/2004 | Satya et al. |
| 6,775,818 B2 | 8/2004 | Taravade et al. |
| 6,777,147 B1 | 8/2004 | Fonseca et al. |
| 6,777,676 B1 | 8/2004 | Wang et al. |
| 6,778,695 B1 | 8/2004 | Schellenberg et al. |
| 6,779,159 B2 | 8/2004 | Yokoyama et al. |
| 6,784,446 B1 | 8/2004 | Phan et al. |
| 6,788,400 B2 | 9/2004 | Chen |
| 6,789,032 B2 | 9/2004 | Barbour et al. |
| 6,803,554 B2 | 10/2004 | Ye et al. |
| 6,806,456 B1 | 10/2004 | Ye et al. |
| 6,807,503 B2 | 10/2004 | Ye et al. |
| 6,813,572 B2 | 11/2004 | Satya et al. |
| 6,820,028 B2 | 11/2004 | Ye et al. |
| 6,828,542 B2 | 12/2004 | Ye et al. |
| 6,842,225 B1 | 1/2005 | Irie et al. |
| 6,859,746 B1 | 2/2005 | Stirton |
| 6,879,403 B2 | 4/2005 | Freifeld |
| 6,879,924 B2 | 4/2005 | Ye et al. |
| 6,882,745 B2 | 4/2005 | Brankner et al. |
| 6,884,984 B2 | 4/2005 | Ye et al. |
| 6,886,153 B1 | 4/2005 | Bevis |
| 6,892,156 B2 | 5/2005 | Ye et al. |
| 6,902,855 B2 | 6/2005 | Peterson et al. |
| 6,906,305 B2 | 6/2005 | Pease et al. |
| 6,918,101 B1 | 7/2005 | Satya et al. |
| 6,919,957 B2 | 7/2005 | Nikoonahad et al. |
| 6,937,753 B1 | 8/2005 | O'Dell et al. |
| 6,948,141 B1 | 9/2005 | Satya et al. |
| 6,959,255 B2 | 10/2005 | Ye et al. |
| 6,966,047 B1 | 11/2005 | Glasser |
| 6,969,837 B2 | 11/2005 | Ye et al. |
| 6,969,864 B2 | 11/2005 | Ye et al. |
| 6,983,060 B1 | 1/2006 | Martinent-Catalot et al. |
| 6,988,045 B2 | 1/2006 | Purdy |
| 6,990,385 B1 | 1/2006 | Smith et al. |
| 7,003,755 B2 | 2/2006 | Pang et al. |
| 7,003,758 B2 | 2/2006 | Ye et al. |
| 7,012,438 B1 | 3/2006 | Miller et al. |
| 7,026,615 B2 | 4/2006 | Takane et al. |
| 7,027,143 B1 | 4/2006 | Stokowski et al. |
| 7,030,966 B2 | 4/2006 | Hansen |
| 7,030,997 B2 | 4/2006 | Neureuther et al. |
| 7,053,355 B2 | 5/2006 | Ye et al. |
| 7,061,625 B1 | 6/2006 | Hwang et al. |
| 7,071,833 B2 | 7/2006 | Nagano et al. |
| 7,103,484 B1 | 9/2006 | Shi et al. |
| 7,106,895 B1 | 9/2006 | Goldberg et al. |
| 7,107,517 B1 | 9/2006 | Suzuki et al. |
| 7,107,571 B2 | 9/2006 | Chang et al. |
| 7,111,277 B2 | 9/2006 | Ye et al. |
| 7,114,143 B2 | 9/2006 | Hanson et al. |
| 7,114,145 B2 | 9/2006 | Ye et al. |
| 7,117,477 B2 | 10/2006 | Ye et al. |
| 7,117,478 B2 | 10/2006 | Ye et al. |
| 7,120,285 B1 | 10/2006 | Spence |
| 7,120,895 B2 | 10/2006 | Ye et al. |
| 7,123,356 B1 | 10/2006 | Stokowski et al. |
| 7,124,386 B2 | 10/2006 | Smith et al. |
| 7,133,548 B2 | 11/2006 | Kenan et al. |
| 7,135,344 B2 | 11/2006 | Nehmadi et al. |
| 7,136,143 B2 | 11/2006 | Smith |
| 7,152,215 B2 | 12/2006 | Smith et al. |
| 7,162,071 B2 | 1/2007 | Hung et al. |
| 7,170,593 B2 | 1/2007 | Honda et al. |
| 7,171,334 B2 | 1/2007 | Gassner |
| 7,174,520 B2 | 2/2007 | White et al. |
| 7,194,709 B2 | 3/2007 | Brankner |
| 7,207,017 B1 | 4/2007 | Tabery et al. |
| 7,231,628 B2 | 6/2007 | Pack et al. |
| 7,236,847 B2 | 6/2007 | Marella |
| 7,271,891 B1 | 9/2007 | Xiong et al. |
| 7,379,175 B2 | 5/2008 | Stokowski et al. |
| 7,383,156 B2 | 6/2008 | Matsusita et al. |
| 7,386,839 B1 | 6/2008 | Golender et al. |
| 7,388,979 B2 | 6/2008 | Sakai et al. |
| 7,418,124 B2 | 8/2008 | Peterson et al. |
| 7,424,145 B2 | 9/2008 | Horie et al. |
| 7,440,093 B1 | 10/2008 | Xiong et al. |
| 7,570,796 B2 | 8/2009 | Zafar et al. |
| 7,676,077 B2 | 3/2010 | Kulkarni et al. |
| 7,683,319 B2 | 3/2010 | Makino et al. |
| 7,738,093 B2 | 6/2010 | Alles et al. |
| 7,739,064 B1 | 6/2010 | Ryker et al. |
| 7,752,584 B2 | 7/2010 | Yang |
| 7,760,929 B2 | 7/2010 | Orbon et al. |
| 7,769,225 B2 | 8/2010 | Kekare et al. |
| 7,774,153 B1 | 8/2010 | Smith |
| 7,877,722 B2 | 1/2011 | Duffy et al. |
| 7,890,917 B1 | 2/2011 | Young et al. |
| 7,904,845 B2 | 3/2011 | Fouquet et al. |
| 7,968,859 B2 | 6/2011 | Young et al. |
| 8,041,103 B2 | 10/2011 | Kulkarni et al. |
| 8,073,240 B2 | 12/2011 | Fischer et al. |
| 8,112,241 B2 | 2/2012 | Xiong |
| 8,126,255 B2 | 2/2012 | Bhaskar et al. |
| 8,204,297 B1 | 6/2012 | Xiong et al. |
| 2001/0017694 A1 | 8/2001 | Oomori et al. |
| 2001/0019625 A1 | 9/2001 | Kenan et al. |
| 2001/0022858 A1 | 9/2001 | Komiya et al. |
| 2001/0043735 A1 | 11/2001 | Smargiassi et al. |
| 2002/0010560 A1 | 1/2002 | Balachandran |
| 2002/0019729 A1 | 2/2002 | Chang et al. |
| 2002/0026626 A1 | 2/2002 | Randall et al. |
| 2002/0033449 A1 | 3/2002 | Nakasuji et al. |
| 2002/0035461 A1 | 3/2002 | Chang et al. |
| 2002/0035641 A1 | 3/2002 | Kurose et al. |
| 2002/0035717 A1 | 3/2002 | Matsuoka |
| 2002/0054291 A1 | 5/2002 | Tsai et al. |
| 2002/0088951 A1 | 7/2002 | Chen |
| 2002/0090746 A1 | 7/2002 | Xu et al. |
| 2002/0134936 A1 | 9/2002 | Matsui et al. |
| 2002/0144230 A1 | 10/2002 | Rittman |
| 2002/0145734 A1 | 10/2002 | Watkins et al. |
| 2002/0164065 A1 | 11/2002 | Cai et al. |
| 2002/0168099 A1 | 11/2002 | Noy |
| 2002/0176096 A1 | 11/2002 | Sentoku et al. |
| 2002/0181756 A1 | 12/2002 | Shibuya et al. |
| 2002/0186878 A1 | 12/2002 | Hoon et al. |
| 2002/0192578 A1 | 12/2002 | Tanaka et al. |
| 2003/0004699 A1 | 1/2003 | Choi et al. |
| 2003/0014146 A1 | 1/2003 | Fujii et al. |
| 2003/0017664 A1 | 1/2003 | Pnueli et al. |
| 2003/0022401 A1 | 1/2003 | Hamamatsu et al. |
| 2003/0033046 A1 | 2/2003 | Yoshitake et al. |
| 2003/0048458 A1 | 3/2003 | Mieher et al. |
| 2003/0048939 A1 | 3/2003 | Lehman |
| 2003/0057971 A1 | 3/2003 | Nishiyama et al. |
| 2003/0076989 A1 | 4/2003 | Maayah et al. |
| 2003/0086081 A1 | 5/2003 | Lehman |
| 2003/0094572 A1 | 5/2003 | Matsui et al. |
| 2003/0098805 A1 | 5/2003 | Bizjak et al. |
| 2003/0128870 A1 | 7/2003 | Pease et al. |
| 2003/0138138 A1 | 7/2003 | Vacca et al. |
| 2003/0138978 A1 | 7/2003 | Tanaka et al. |
| 2003/0169916 A1 | 9/2003 | Hayashi et al. |
| 2003/0173516 A1 | 9/2003 | Takane et al. |
| 2003/0192015 A1 | 10/2003 | Liu |
| 2003/0207475 A1 | 11/2003 | Nakasuji et al. |
| 2003/0223639 A1 | 12/2003 | Shlain et al. |
| 2003/0226951 A1 | 12/2003 | Ye et al. |
| 2003/0227620 A1 | 12/2003 | Yokoyama et al. |
| 2003/0228714 A1 | 12/2003 | Smith et al. |
| 2003/0229410 A1 | 12/2003 | Smith et al. |
| 2003/0229412 A1 | 12/2003 | White et al. |

(56) References Cited

U.S. PATENT DOCUMENTS

| | | |
|---|---|---|
| 2003/0229868 A1 | 12/2003 | White et al. |
| 2003/0229875 A1 | 12/2003 | Smith et al. |
| 2003/0229880 A1 | 12/2003 | White et al. |
| 2003/0229881 A1 | 12/2003 | White et al. |
| 2003/0237064 A1 | 12/2003 | White et al. |
| 2004/0030430 A1 | 2/2004 | Matsuoka |
| 2004/0032908 A1 | 2/2004 | Hagai et al. |
| 2004/0049722 A1 | 3/2004 | Matsushita |
| 2004/0052411 A1 | 3/2004 | Qian et al. |
| 2004/0057611 A1 | 3/2004 | Lee et al. |
| 2004/0066506 A1 | 4/2004 | Elichai et al. |
| 2004/0091142 A1 | 5/2004 | Peterson et al. |
| 2004/0094762 A1 | 5/2004 | Hess et al. |
| 2004/0098216 A1 | 5/2004 | Ye et al. |
| 2004/0102934 A1 | 5/2004 | Chang |
| 2004/0107412 A1 | 6/2004 | Pack et al. |
| 2004/0119036 A1 | 6/2004 | Ye et al. |
| 2004/0120569 A1 | 6/2004 | Hung et al. |
| 2004/0133369 A1 | 7/2004 | Pack et al. |
| 2004/0147121 A1 | 7/2004 | Nakagaki et al. |
| 2004/0174506 A1 | 9/2004 | Smith |
| 2004/0179738 A1 | 9/2004 | Dai et al. |
| 2004/0199885 A1 | 10/2004 | Lu et al. |
| 2004/0223639 A1 | 11/2004 | Sato et al. |
| 2004/0228515 A1 | 11/2004 | Okabe et al. |
| 2004/0234120 A1 | 11/2004 | Honda et al. |
| 2004/0243320 A1 | 12/2004 | Chang et al. |
| 2004/0246476 A1 | 12/2004 | Bevis et al. |
| 2004/0254752 A1 | 12/2004 | Wisniewski et al. |
| 2005/0004774 A1 | 1/2005 | Volk et al. |
| 2005/0008218 A1 | 1/2005 | O'Dell et al. |
| 2005/0010890 A1 | 1/2005 | Nehmadi et al. |
| 2005/0013474 A1 | 1/2005 | Sim |
| 2005/0062962 A1 | 3/2005 | Fairley et al. |
| 2005/0069217 A1 | 3/2005 | Mukherjee |
| 2005/0117796 A1 | 6/2005 | Matsui et al. |
| 2005/0132306 A1 | 6/2005 | Smith et al. |
| 2005/0141764 A1 | 6/2005 | Tohyama et al. |
| 2005/0166174 A1 | 7/2005 | Ye et al. |
| 2005/0184252 A1 | 8/2005 | Ogawa et al. |
| 2005/0190957 A1 | 9/2005 | Cai et al. |
| 2005/0198602 A1 | 9/2005 | Brankner et al. |
| 2006/0000964 A1 | 1/2006 | Ye et al. |
| 2006/0036979 A1 | 2/2006 | Zurbrick et al. |
| 2006/0038986 A1 | 2/2006 | Honda et al. |
| 2006/0048089 A1 | 3/2006 | Schwarzband |
| 2006/0051682 A1 | 3/2006 | Hess et al. |
| 2006/0062445 A1 | 3/2006 | Verma et al. |
| 2006/0066339 A1 | 3/2006 | Rajski et al. |
| 2006/0082763 A1 | 4/2006 | Teh et al. |
| 2006/0159333 A1 | 7/2006 | Ishikawa |
| 2006/0161452 A1 | 7/2006 | Hess |
| 2006/0193506 A1 | 8/2006 | Dorphan et al. |
| 2006/0193507 A1 | 8/2006 | Sali et al. |
| 2006/0236294 A1 | 10/2006 | Saidin et al. |
| 2006/0236297 A1 | 10/2006 | Melvin, III et al. |
| 2006/0239536 A1 | 10/2006 | Shibuya et al. |
| 2006/0265145 A1 | 11/2006 | Huet et al. |
| 2006/0266243 A1 | 11/2006 | Percin et al. |
| 2006/0269120 A1 | 11/2006 | Nehmadi et al. |
| 2006/0273242 A1 | 12/2006 | Hunsche et al. |
| 2006/0273266 A1 | 12/2006 | Preil et al. |
| 2006/0277520 A1 | 12/2006 | Gennari |
| 2006/0291714 A1 | 12/2006 | Wu et al. |
| 2006/0292463 A1 | 12/2006 | Best et al. |
| 2007/0002322 A1 | 1/2007 | Borodovsky et al. |
| 2007/0011628 A1 | 1/2007 | Ouali et al. |
| 2007/0013901 A1 | 1/2007 | Kim et al. |
| 2007/0019171 A1 | 1/2007 | Smith |
| 2007/0019856 A1 | 1/2007 | Furman |
| 2007/0031745 A1 | 2/2007 | Ye et al. |
| 2007/0032896 A1 | 2/2007 | Ye et al. |
| 2007/0035322 A1 | 2/2007 | Kang et al. |
| 2007/0035712 A1 | 2/2007 | Gassner et al. |
| 2007/0035728 A1 | 2/2007 | Kekare et al. |
| 2007/0052963 A1 | 3/2007 | Orbon et al. |
| 2007/0064995 A1 | 3/2007 | Oaki et al. |
| 2007/0133860 A1 | 6/2007 | Lin et al. |
| 2007/0156379 A1 | 7/2007 | Kulkarni et al. |
| 2007/0230770 A1 | 10/2007 | Kulkarni et al. |
| 2007/0248257 A1 | 10/2007 | Bruce et al. |
| 2007/0280527 A1 | 12/2007 | Almogy et al. |
| 2007/0288219 A1 | 12/2007 | Zafar et al. |
| 2008/0013083 A1 | 1/2008 | Kirk et al. |
| 2008/0015802 A1 | 1/2008 | Urano et al. |
| 2008/0016481 A1 | 1/2008 | Matsuoka et al. |
| 2008/0018887 A1 | 1/2008 | Chen et al. |
| 2008/0049994 A1 | 2/2008 | Rognin et al. |
| 2008/0058977 A1 | 3/2008 | Honda |
| 2008/0072207 A1 | 3/2008 | Verma et al. |
| 2008/0081385 A1 | 4/2008 | Marella et al. |
| 2008/0163140 A1 | 7/2008 | Fouquet et al. |
| 2008/0167829 A1 | 7/2008 | Park et al. |
| 2008/0250384 A1 | 10/2008 | Duffy et al. |
| 2008/0295047 A1 | 11/2008 | Nehmadi et al. |
| 2008/0295048 A1 | 11/2008 | Nehmadi et al. |
| 2008/0304056 A1 | 12/2008 | Alles et al. |
| 2009/0024967 A1 | 1/2009 | Su et al. |
| 2009/0037134 A1 | 2/2009 | Kulkarni et al. |
| 2009/0041332 A1 | 2/2009 | Bhaskar et al. |
| 2009/0043527 A1 | 2/2009 | Park et al. |
| 2009/0055783 A1 | 2/2009 | Florence et al. |
| 2009/0067703 A1 | 3/2009 | Lin et al. |
| 2009/0080759 A1 | 3/2009 | Bhaskar et al. |
| 2009/0210183 A1 | 8/2009 | Rajski et al. |
| 2009/0257645 A1 | 10/2009 | Chen et al. |
| 2009/0284733 A1 | 11/2009 | Wallingford et al. |
| 2009/0290782 A1 | 11/2009 | Regensburger |
| 2009/0299681 A1 | 12/2009 | Chen et al. |
| 2009/0323052 A1 | 12/2009 | Silberstein et al. |
| 2010/0142800 A1 | 6/2010 | Pak et al. |
| 2010/0146338 A1 | 6/2010 | Schalick et al. |
| 2010/0150429 A1 | 6/2010 | Jau et al. |
| 2010/0188657 A1 | 7/2010 | Chen et al. |
| 2010/0226562 A1 | 9/2010 | Wu et al. |
| 2011/0013825 A1 | 1/2011 | Shibuya et al. |
| 2011/0052040 A1 | 3/2011 | Kuan |
| 2011/0184662 A1 | 7/2011 | Badger et al. |
| 2011/0251713 A1 | 10/2011 | Teshima et al. |
| 2011/0276935 A1 | 11/2011 | Fouquet et al. |
| 2011/0311126 A1 | 12/2011 | Sakai et al. |
| 2012/0308112 A1 | 12/2012 | Hu et al. |
| 2012/0319246 A1 | 12/2012 | Tan et al. |
| 2013/0009989 A1 | 1/2013 | Chen et al. |
| 2013/0027196 A1 | 1/2013 | Yankun et al. |

FOREIGN PATENT DOCUMENTS

| | | |
|---|---|---|
| CN | 1646896 | 7/2005 |
| EP | 0032197 | 7/1981 |
| EP | 0370322 | 5/1990 |
| EP | 1061358 | 12/2000 |
| EP | 1061571 | 12/2000 |
| EP | 1065567 | 1/2001 |
| EP | 1066925 | 1/2001 |
| EP | 1069609 | 1/2001 |
| EP | 1093017 | 4/2001 |
| EP | 1329771 | 7/2003 |
| EP | 1480034 | 11/2004 |
| EP | 1696270 | 8/2006 |
| JP | 7-159337 | 6/1995 |
| JP | 2002-071575 | 3/2002 |
| JP | 2002-365235 | 12/2002 |
| JP | 2003-215060 | 7/2003 |
| JP | 2004-045066 | 2/2004 |
| JP | 2005-283326 | 10/2005 |
| JP | 2007-234798 | 9/2007 |
| JP | 2009-122046 | 6/2009 |
| JP | 2010-256242 | 11/2010 |
| JP | 2012-225768 | 11/2012 |
| KR | 10-2001-0007394 | 1/2001 |
| KR | 10-2001-0037026 | 5/2001 |
| KR | 10-2001-0101697 | 11/2001 |
| KR | 10-2003-0055848 | 7/2003 |

(56) References Cited

FOREIGN PATENT DOCUMENTS

| | | |
|---|---|---|
| KR | 10-2006-0075691 | 7/2005 |
| KR | 10-2005-0092053 | 9/2005 |
| KR | 10-2006-0124514 | 12/2006 |
| KR | 10-0696276 | 3/2007 |
| KR | 10-2010-0061018 | 6/2010 |
| KR | 10-2012-0068128 | 6/2012 |
| WO | 98/57358 | 12/1998 |
| WO | 99/22310 | 5/1999 |
| WO | 99/25004 | 5/1999 |
| WO | 99/59200 | 5/1999 |
| WO | 99/38002 | 7/1999 |
| WO | 99/41434 | 8/1999 |
| WO | 00/03234 | 1/2000 |
| WO | 00/36525 | 6/2000 |
| WO | 00/55799 | 9/2000 |
| WO | 00/68884 | 11/2000 |
| WO | 00/70332 | 11/2000 |
| WO | 01/09566 | 2/2001 |
| WO | 01/40145 | 6/2001 |
| WO | 03/104921 | 12/2003 |
| WO | 2004/027684 | 4/2004 |
| WO | 2004/097903 | 11/2004 |
| WO | 2006/012388 | 2/2006 |
| WO | 2006/063268 | 6/2006 |
| WO | 2009/152046 | 9/2009 |
| WO | 2010/093733 | 8/2010 |

OTHER PUBLICATIONS

U.S. Appl. No. 60/684,360, filed May 24, 2005 by Nehmadi et al.
U.S. Appl. No. 13/652,377, filed Oct. 15, 2012 by Wu et al.
Allan et al., "Critical Area Extraction for Soft Fault Estimation," IEEE Transactions on Semiconductor Manufacturing, vol. 11, No. 1, Feb. 1998.
Barty et al., "Aerial Image Microscopes for the inspection of defects in EUV masks," Proceedings of SPIE, vol. 4889, 2002, pp. 1073-1084.
Budd et al., "A New Mask Evaluation Tool, the Microlithography Simulation Microscope Aerial Image Measurement System," SPIE vol. 2197, 1994, pp. 530-540.
Cai et al., "Enhanced Dispositioning of Reticle Defects Using the Virtual Stepper With Automoated Defect Severity Scoring," Proceedings of the SPIE, vol. 4409, Jan. 2001, pp. 467-478.
Comizzoli, "Uses of Corona Discharges in the Semiconductor Industry," J. Electrochem. Soc., 1987, pp. 424-429.
Contactless Electrical Equivalent Oxide Thickness Measurement, IBM Technical Disclosure Bulletin, vol. 29, No. 10, 1987, pp. 4622-4623.
Contactless Photovoltage vs. Bias Method for Determining Flat-Band Voltage, IBM Technical Disclosure Bulletin, vol. 32, vol. 9A, 1990, pp. 14-17.
Cosway et al., "Manufacturing Implementation of Corona Oxide Silicon (COS) Systems for Diffusion Furnace Contamination Monitoring," 1997 IEEE/SEMI Advanced Semiconductor Manufacturing Conference, pp. 98-102.
Diebold et al., "Characterization and produiction metrology of thin transistor gate oxide films," Materials Science in Semiconductor Processing 2, 1999, pp. 103-147.
Dirksen et al., "Impact of high order aberrations on the performance of the aberration monitor," Proc. Of SPIE vol. 4000, Mar. 2000, pp. 9-17.
Dirksen et al., "Novel aberration monitor for optical lithography," Proc. Of SPIE vol. 3679, Jul. 1999, pp. 77-86.
Garcia et al., "New Die to Database Inspection Algorithm for Inspection of 90-nm Node Reticles," Proceedings of SPIE, vol. 5130, 2003, pp. 364-374.
Granik et al., "Sub-resolution process windows and yield estimation technique based on detailed full-chip CD simulation," Mentor Graphics, Sep. 2000, 5 pages.
Hess et al., "A Novel Approach: High Resolution Inspection with Wafer Plane Defect Detection," Proceedings of SPIE—International Society for Optical Engineering; Photomask and Next-Generation Lithography Mask Technology 2008, vol. 7028, 2008.
Huang et al., "Process Window Impact of Progressive Mask Defects, Its Inspection and Disposition Techniques (go/no-go criteria) Via a Lithographic Detector," Proceedings of SPIE—The International Society for Optical Engineering; 25th Annual Bacus Symposium on Photomask Technology 2005, vol. 5992, No. 1, 2005, p. 6.
Huang et al., "Using Design Based Binning to Improve Defect Excursion Control for 45nm Production," IEEE, International Symposium on Semiconductor Manufacturing, Oct. 2007, pp. 1-3.
Hung et al., Metrology Study of Sub 20 Angstrom oxynitride by Corona-Oxide-Silicon (COS) and Conventional C-V Approaches, 2002, Mat. Res. Soc. Symp. Proc., vol. 716, pp. 119-124.
Karklin et al., "Automatic Defect Severity Scoring for 193 nm Reticle Defect Inspection," Proceedings of SPIE—The International Society for Optical Engineering, 2001, vol. 4346, No. 2, pp. 898-906.
Lo et al., "Identifying Process Window Marginalities of Reticle Designs for 0.15/0.13 μm Technologies," Proceedings of SPIE vol. 5130, 2003, pp. 829-837.
Lorusso et al. "Advanced DFM Applns. Using design-based metrology on CDSEM," SPIE vol. 6152, Mar. 27, 2006.
Lu et al., "Application of Simulation Based Defect Printability Analysis for Mask Qualification Control," Proceedings of SPIE, vol. 5038, 2003, pp. 33-40.
Mack, "Lithographic Simulation: A Review," Proceedings of SPIE vol. 4440, 2001, pp. 59-72.
Martino et al., "Application of the Aerial Image Measurement System (AIMS(TM)) to the Analysis of Binary Mask Imaging and Resolution Enhancement Techniques," SPIE vol. 2197, 1994, pp. 573-584.
Miller, "A New Approach for Measuring Oxide Thickness," Semiconductor International, Jul. 1995, pp. 147-148.
Nagpal et al., "Wafer Plane Inspection for Advanced Reticle Defects," Proceedings of SPIE—The International Society for Optical Engineering; Photomask and Next-Generation Lithography Mask Technology. vol. 7028, 2008.
Numerical Recipes in C. The Art of Scientific Computing, 2nd Ed., @ Cambridge University Press 1988, 1992, p. 683.
O'Gorman et al., "Subpixel Registration Using a Concentric Ring Fiducial," Proceedings of the International Conference on Pattern Recognition, vol. ii, Jun. 16, 1990, pp. 249-253.
Otsu, "A Threshold Selection Method from Gray-Level Histograms," IEEE Transactions on Systems, Man, and Cybernetics, vol. SMC-9, No. 1, Jan. 1979, pp. 62-66.
Pang et al., "Simulation-based Defect Printability Analysis on Alternating Phase Shifting Masks for 193 nm Lithography," Proceedings of SPIE, vol. 4889, 2002, pp. 947-954.
Pettibone et al., "Wafer Printability Simulation Accuracy Based on UV Optical Inspection Images of Reticle Defects," Proceedings of SPIE—The International Society for Optical Engineering 1999 Society of Photo-Optical Instrumentation Engineers, vol. 3677, No. II, 1999, pp. 711-720.
Phan et al., "Comparison of Binary Mask Defect Printability Analysis Using Virtual Stepper System and Aerial Image Microscope System," Proceedings of SPIE—The International Society for Optical Engineering 1999 Society of Photo-Optical Instrumentation Engineers, vol. 3873, 1999, pp. 681-692.
Sahouria et al., "Full-chip Process Simulation for Silicon DRC," Mentor Graphics, Mar. 2000, 6 pages.
Sato et al., "Defect Criticality Index (DCI): A new methodology to significantly improve DOI sampling rate in a 45nm production environment," Metrology, Inspection, and Process Control for Microlithography XXII, Proc. Of SPIE vol. 6922, 692213 (2008), pp. 1-9.
Schroder et al., Corona-Oxide-Semiconductor Device Characterization, 1998, Solid-State Electronics, vol. 42, No. 4, pp. 505-512.
Schroder, "Surface voltage and surface photovoltage: history, theory and applications," Measurement Science and Technology, vol. 12, 2001, pp. R16-31.
Schroder, Contactless Surface Charge Semiconductor Characterization, Apr. 2002, Materials Science and Engineering B, vol. 91-92, pp. 196-228.

(56) References Cited

OTHER PUBLICATIONS

Schurz et al., "Simulation Study of Reticle Enhancement Technology Applications for 157 nm Lithography," SPIE vol. 4562, 2002, pp. 902-913.

Svidenko et al. "Dynamic Defect-Limited Yield Prediction by Criticality Factor," ISSM Paper: YE-O-157, 2007.

Tang et al., "Analyzing Volume Diagnosis Results with Statistical Learning for Yield Improvement" 12th IEEE European Test Symposium, Freiburg 2007, IEEE European, May 20-24, 2007, pp. 145-150.

Verkuil et al., "A Contactless Alternative to MOS Charge Measurements by Means of a Corona-Oxide-Semiconductor (COS) Technique," Electrochem. Soc. Extended Abstracts, 1988, vol. 88-1, No. 169, pp. 261-262.

Verkuil, "Rapid Contactless Method for Measuring Fixed Oxide Charge Associated with Silicon Processing," IBM Technical Disclosure Bulletin, vol. 24, No. 6, 1981, pp. 3048-3053.

Volk et al. "Investigation of Reticle Defect Formation at DUV Lithography," 2002, BACUS Symposium on Photomask Technology.

Volk et al. "Investigation of Reticle Defect Formation at DUV Lithography," 2003, IEEE/SEMI Advanced Manufacturing Conference, pp. 29-35.

Volk et al., "Investigation of Smart Inspection of Critical Layer Reticles using Additional Designer Data to Determine Defect Significance," Proceedings of SPIE vol. 5256, 2003, pp. 489-499.

Weinberg, "Tunneling of Electrons from Si into Thermally Grown SiO2," Solid-State Electronics, 1977, vol. 20, pp. 11-18.

Weinzierl et al., "Non-Contact Corona-Based Process Control Measurements: Where We've Been, Where We're Headed," Electrochemical Society Proceedings, Oct. 1999, vol. 99-16, pp. 342-350.

Yan et al., "Printability of Pellicle Defects in DUV 0.5 urn Lithography," SPIE vol. 1604, 1991, pp. 106-117.

Guo et al., "License Plate Localization and Character Segmentation with Feedback Self-Learning and Hybrid Binarization Techniques," IEEE Transactions on Vehicular Technology, vol. 57, No. 3, May 2008, pp. 1417-1424.

Liu, "Robust Image Segmentation Using Local Median," Proceedings of the 3rd Canadian Conference on Computer and Robot Vision (CRV'06) 0-7695-2542-3/06, 2006 IEEE, 7 pages total.

International Search Report and Written Opinion for PCT/US2014/010352 mailed Apr. 29, 2014.

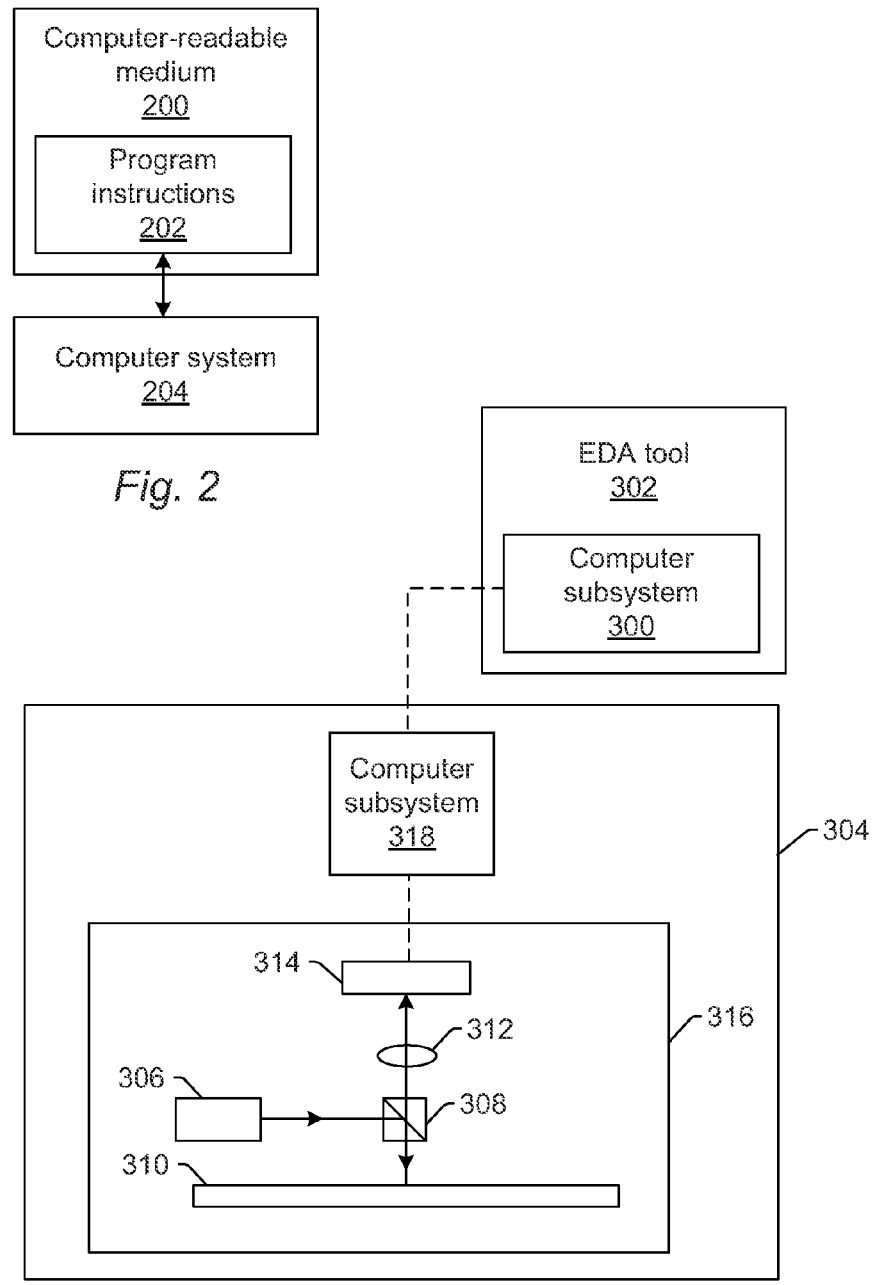

DETERMINING A POSITION OF INSPECTION SYSTEM OUTPUT IN DESIGN DATA SPACE

BACKGROUND OF THE INVENTION

1. Field of the Invention

The present invention generally relates to systems and methods for determining a position of output of an inspection system in design data space.

2. Description of the Related Art

The following description and examples are not admitted to be prior art by virtue of their inclusion in this section.

Inspection processes are used at various steps during a semiconductor manufacturing process to detect defects on wafers to promote higher yield in the manufacturing process and thus higher profits. Inspection has always been an important part of fabricating semiconductor devices such as ICs. However, as the dimensions of semiconductor devices decrease, inspection becomes even more important to the successful manufacture of acceptable semiconductor devices because smaller defects can cause the devices to fail. For instance, as the dimensions of semiconductor devices decrease, detection of defects of decreasing size has become necessary since even relatively small defects may cause unwanted aberrations in the semiconductor devices.

Some currently available inspection systems are configured to use user-defined alignment marks on each die row to orient themselves to the wafer. In each swath, individual dies are compared with adjacent dies through constant feedback in order to ensure that each die looks identical. The locations in any given swath are remarkably accurate. That is, if one were to visit the same die relative location on multiple dies of the same swath, then one is likely to find the same feature.

However, an entire swath may be misplaced in relation to a global (design) coordinate system. Defect location accuracy for inspection can be improved drastically if the swath positioning errors relative to design can be computed and eliminated from each swath. There are currently available technologies that can be used to compare wafer images to the underlying design and estimate the swath positioning errors. The main disadvantage of such technologies is that they require a customer or the design owner to provide the device manufacturer and/or wafer inspector with the design files for the devices that are being manufactured. It is difficult and sometimes impossible for a customer or design owner to provide the device manufacturer and/or wafer inspector with design information due to the presence of sensitive intellectual property (IP)-related information in the design files.

Accordingly, it would be advantageous to develop systems and methods for determining a position of output of an inspection system in design data space that do not have one or more of the disadvantages described above.

SUMMARY OF THE INVENTION

The following description of various embodiments is not to be construed in any way as limiting the subject matter of the appended claims.

One embodiment relates to a method for determining a position of output of an inspection system in design data space. The method includes merging more than one feature in design data space for a wafer into a single feature that has a periphery that encompasses all of the features that are merged. The method also includes storing information for the single feature without the design data for the features that are merged. The information includes a position of the single feature in design data space. In addition, the method includes aligning output of an inspection system for the wafer to the information for the single feature and determining a position of a first portion of the output aligned to the single feature in the design data space based on the position of the single feature in the design data space. The method further includes determining positions in the design data space of other portions of the output based on the position of the first portion of the output in the design data space. The merging step, the storing step, the aligning step, determining the position of the first portion of the output, and determining the positions of the other portions are performed by one or more computer systems.

Each of the steps of the method may be further performed as described herein. In addition, the method may include any other step(s) of any other method(s) described to herein. Furthermore, the method may be performed by any of the systems described herein.

Another embodiment relates to a method for determining a position of output of an inspection system in design data space. The method includes aligning output of an inspection system for a wafer to information for a single feature. More than one feature in design data for the wafer were merged into the single feature that has a periphery that encompasses all of the features that were merged. The information includes a position of the single feature in design data space. The method also includes determining a position of a first portion of the output aligned to the single feature in the design data space based on the position of the single feature in the design data space. In addition, the method includes determining positions in the design data space of other portions of the output based on the position of the first portion of the output in the design data space. Aligning the output, determining the position of the first portion of the output, and determining the positions of the other portions are performed using a computer system.

Each of the steps of the method may be further performed as described herein. In addition, the method may include any other step(s) of any other method(s) described herein. Furthermore, the method may be performed by any of the systems described herein.

An additional embodiment relates to a system configured to determine a position of output of an inspection system in design data space. The system includes a computer subsystem configured for merging more than one feature in design data for a wafer into a single feature that has a periphery that encompasses all of the features that are merged. The computer subsystem is also configured for storing information for the single feature without the design data for the features that are merged. The information includes a position of the single feature in design data space. The system also includes an inspection subsystem configured for scanning the wafer to generate output for the wafer. The inspection subsystem is also configured for aligning the output, determining a position of a first portion of the output, and determining positions of other portions of the output as described above. The system may be further configured as described herein.

BRIEF DESCRIPTION OF THE DRAWINGS

Further advantages of the present invention will become apparent to those skilled in the art with the benefit of the following detailed description of the preferred embodiments and upon reference to the accompanying drawings in which:

FIG. 2 is a block diagram illustrating one embodiment of a non-transitory computer-readable medium storing program instructions for causing a computer system to perform a computer-implemented method described herein; and FIG. 3 is a schematic diagram illustrating a side view of an embodiment of a system configured to determine a position of output of an inspection system in design data space.

Figure 1:
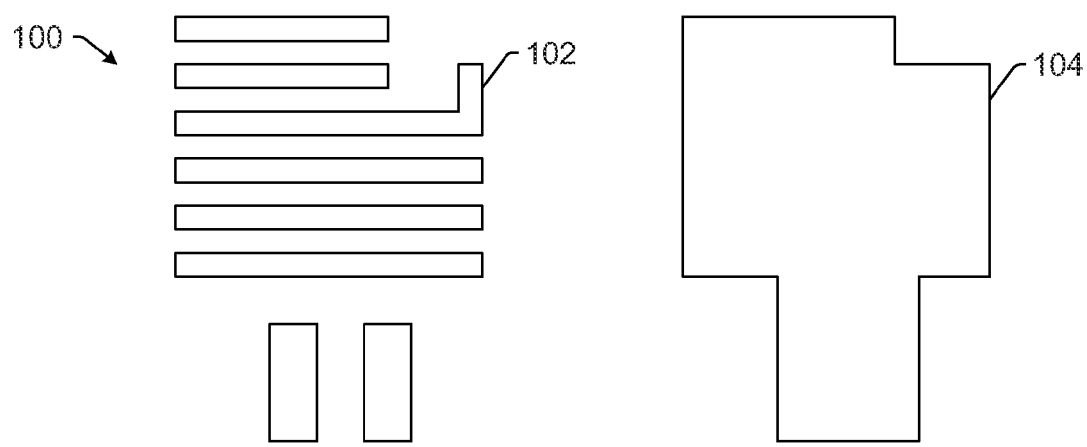
FIG. 1 is a schematic diagram illustrating a step that may be included in some embodiments of the methods described herein.

While the invention is susceptible to various modifications and alternative forms, specific embodiments thereof are shown by way of example in the drawings and may herein be described in detail. The drawings may not be to scale. It should be understood, however, that the drawings and detailed description thereto are not intended to limit the invention to the particular form disclosed, but on the contrary, the intention is to cover all modifications, equivalents and alternatives falling within the spirit and scope of the present invention as defined by the appended claims.

DETAILED DESCRIPTION OF THE PREFERRED EMBODIMENTS

Turning now to the drawings, it is noted that the figures are not drawn to scale. In to particular, the scale of some of the elements of the figures is greatly exaggerated to emphasize characteristics of the elements. It is also noted that the figures are not drawn to the same scale. Elements shown in more than one figure that may be similarly configured have been indicated using the same reference numerals. Unless otherwise noted herein, any of the elements described and shown may include any suitable commercially available elements.

One embodiment relates to a method for determining a position of output of an inspection system in design data space. In one embodiment, the inspection system is configured as a bright field (BF) inspection system. The inspection system may be configured as described further herein. Since the embodiments described herein determine the position of inspection output, which in the case of image output may include pixels, in design data space, the embodiments may be generally referred to as pixel-to-design alignment (PDA) systems or methods.

The term "design data" as used herein generally refers to the physical design (layout) of an IC and data derived from the physical design through complex simulation or simple geometric and Boolean operations. The design data may be stored in a data structure such as a graphical data stream (GDS) file, any other standard machine-readable file, any other suitable file known in the art, and a design database. A GDSII file is one of a class of files used for the representation of design layout data. Other examples of such files include GL1 and OASIS files. The design data used in the embodiments described herein may be stored in any of this entire class of files irrespective of data structure configuration, storage format, or storage mechanism.

The method includes merging more than one feature in design data for a wafer into a single feature that has a periphery that encompasses all of the features that are merged. Therefore, merging the more than one feature into the single feature may create a derivative of the design for the wafer. In one embodiment, as shown in FIG. 1, the design data may include original design artifact 100 that includes a number of features 102. These features 102 may be merged into single feature 104, which is then the to derived design or the derivative of the design. In the derived design, any feature that is relatively close to any other feature may be merged to create a derivative of design. Features that are relatively close to one another may include any features in the design other than isolated features.

In one embodiment, the single feature includes a bounding polygon defining the periphery of the single feature, the single feature includes no additional features within its periphery, and the bounding polygon contains no additional polygons. For example, as shown in FIG. 1, the single feature may not include features 102 that were merged to create the single feature or any other features. In other words, single feature 104 is a polygon that has a periphery defining its shape. The periphery of the single feature is defined by generating a polygon that encompasses all of the features that were merged. The features that are merged are not, however, included in the single feature. In addition, as shown in FIG. 1, the bounding polygon that defines the single feature does not contain any additional polygons within its boundary. As further shown in FIG. 1, the single feature may be defined be a single polygon and may be different (e.g., different in shape, size, etc.) than each of the features that were merged to create the single feature.

In some embodiments, merging the more than one feature eliminates intellectual property (IP) in the design data from the information for the single feature. For example, creating a derivative of the design as described above can be performed to remove all IP sensitive information from the design file. In the example shown in FIG. 1, the particulars of the patterns contained in the original design artifact 100 and the placement of these patterns may be IP information. In the derived design, any feature that is relatively close to any other feature may be merged to create a derivative of the design that destroys the IP in an unrecoverable manner. For example, as described above, the merged features are not included in the design derivative. In addition, all critical structures in the design may be replaced in the merging step with bounding boxes or polygons around them. Therefore, other steps described herein that are performed with the information for the single feature can be performed without the need for IP sensitive design information. As such, any of those steps can be performed without compromising or exposing any IP sensitive design information.

In another embodiment, the features that are merged have at least one lateral dimension (e.g., a width) on the wafer that is less than 100 nm, and the inspection system is not capable of resolving features printed on the wafer having a lateral dimension (e.g., a width) that is less than 200 nm. Design rules are constantly shrinking. A 22 nm design rule design typically manifests (is printed) on wafers as features that are slightly bigger (40 nm or so) on the wafers. While the design rules are shrinking, the inspection wavelengths are not keeping pace. The wavelengths of light that are used for inspecting wafers are still around 200 nm or higher. The implication of the relationship between feature size and inspection wavelength is that BF inspection tools fail to resolve a lot of critical design details that are put on the wafer by the designer or design owner. For example, most BF inspection tools resolve features that are about 250 nm to about 300 nm or greater. Although wafer inspection systems fail to resolve many features formed on wafers, inspection system manufacturers such as KLA-Tencor, Milpitas, Calif. have found innovative ways to detect defects in these areas thereby providing continuing value to their customers.

A fundamental insight of the embodiments described herein is that since patterns that are substantially small (e.g., less than 200 nm) are not resolved, design data for such substantially small patterns is not needed to align swaths of output to the underlying design. In other words, intricate design details that may be IP sensitive design features may be below the resolution limit of the inspection system. Therefore, those features are essentially useless for alignment and can be eliminated as described herein. For example, in the merging step described above, the original design may be modified to remove IP sensitive information by merging any design artifact that is thinner than the optical resolution limit of the inspection system. In the example shown in FIG. 1, since the optical image of pattern 100 that would be produced by most wafer inspection systems would look like single feature 104, the IP-less version of the design is sufficient for aligning the output of the inspection system accurately to the design data. In this manner, in cases in which the design rule is 22 nm and the optical resolution limit of the inspection system is 300 nm, IP sensitive information can be effectively eliminated. In addition, the alignment that can be performed using bounding polygons that replace intricate design patterns in the merging step should have no appreciable difference in accuracy as the alignment that can be performed using the intricate design patterns.

In some embodiments, the features that are merged include dense features in the design data. For example, the merging step may include replacing all dense lines with their bounding polygons. In one such example, as described above, in the derived design, any feature that is relatively close to any other feature may be merged to create a derivative of design, and features that are relatively close to one another may include any features in the design other than isolated features. The terms "dense features" and "isolated features" are commonly used in the art to indicate different types of features typically included in design data for wafers.

In another embodiment, the features that are merged include features in a random logic area of the design data. For example, the inspection system resolution limits described above may make defect detection in random logic areas a bit more difficult than other areas on the wafer such as array regions. However, this lack of resolution in the random logic areas could be a boon for coordinate accuracy. For example, the random logic areas may contain features that can be merged as described herein to form single features that are relatively unique (e.g., have odd shapes) making them particularly useful as alignment marks when formed on wafers. Any of the features that are merged in the embodiments described herein may include device features as opposed to non-device features such as reticle alignment marks and features that will be printed in a non-device area of the wafer. The term "random logic area" is a known term commonly used in the art and is intended to have the customary meaning in the art.

In some embodiments, merging the more than one feature includes merging two or more sets of more than one feature in the design data into corresponding single features, and the method includes selecting the single feature whose information will be used in the aligning step described further herein from the corresponding single features. For example, different single features may be created during the merging step described above from different sets of features in the design data. The features that are merged into any one single feature may be mutually exclusive of the features that are merged into any other single feature. In this manner, the merging step may be performed more than once to create more than one single feature. Information for those different single features such as their bounding polygons and other non-IP sensitive alignment targets from the design data may be stored as described further herein in an "alignment file," which may essentially be a design file containing no IP since the merging step may be performed to remove any sensitive IP from the design. Selecting the single feature that will be used for alignment may include using an inspection system to find one or more good alignment spots from among the different single features and other non-IP sensitive alignment targets by searching this design file. Single features may qualify as "good alignment spots" if they are different enough from surrounding and nearby features to be uniquely identified in inspection system output and can be resolved with relatively good quality by the inspection system. The surrounding and nearby features from which a single feature must be different enough to qualify as a "good alignment spot" may vary depending on characteristics of the inspection system such as field of view and wafer/stage alignment capability. Wafer image(s) may then be extracted for the good alignment spot(s) and stored as described further herein such that they can be used in the aligning step described further herein.

In one embodiment, merging the more than one feature includes merging two or more sets of more than one feature in the design data into corresponding single features, the storing step described further herein includes storing information for the corresponding single features without the design data for the features that are merged, and the method includes selecting the single feature whose information will be used in the aligning step by acquiring output of the inspection system at locations of the corresponding single features on the wafer and selecting one of the corresponding single features that will provide more accurate alignment than others of the corresponding single features. For example, as described above, the merging step may include replacing to dense lines with their bounding polygons or otherwise creating more than one of the single features, and information for each of the more than one single feature can be stored in the storing step described further herein without the design data for the features merged to create the single features. The inspection system may then be used to generate output such as wafer image(s) for the wafer, and the method may include finding good alignment spots in the wafer image(s), which may be performed in any suitable manner. Alignment spots that are "good" may be defined as described above. Image(s) acquired by the inspection system at the locations of the good alignment spot(s) may then be stored with the information for the single feature(s) in the storing step described further herein.

In some embodiments, the method includes simulating output that will be produced for the single feature by the inspection system based on the information for the single feature. For example, design clips of the location(s) of the good alignment spot(s) identified above may be extracted from the modified design (i.e., the information for the corresponding single features) and rendered to look like the wafer image that was produced by the inspection system or that will be produced by the inspection system. The rendered image(s) may then be sent back to the inspection system and used during alignment, which may be performed as described further herein, to improve the coordinate accuracy of the inspection system.

The method also includes storing information for the single feature without the design data for the features that are merged. The information includes a position of the single feature in design data space. The information for the position of the single feature in the design data space may, therefore, be design data coordinates for the single feature.

The information for the single feature may also include a modified version of the design that includes any information for any single features that were created. This modified version of the design will then not include any sensitive IP information and can be stored in a computer-readable storage medium such as those described further herein. As such, the modified design may be stored without sensitive IP.

The information for the single feature may be stored in a computer-readable storage medium different than the one from which the design data was acquired for use in the embodiments described herein. For example, in one embodiment, storing the information includes storing the information in a storage medium in which the design data is not stored. Therefore, when a system, method, or user accesses and/or uses the stored information from the storage medium, the system, method, or user may not be able to access and/or use the design data containing potentially sensitive IP since it is not stored in that storage medium. In addition, the information for the single feature(s) and the design data may be stored in different data structures (e.g., files) in the same storage medium. In this manner, the modified design and the original design may be stored in a number of different manners as long as the modified design can be accessed and used without needing to access and/or use the original design.

In some embodiments, the method includes identifying isolated features in the design data, and the information that is stored does not includes the design data for the isolated features. For example, the method may include eliminating all isolated lines or other isolated features in the design data, which may be performed prior to the merging step described above, during the merging step, or after the merging step. For example, prior to the merging step, the design data may be scanned for any isolated features. Those features may be removed from the design data, and then any remaining dense features may be merged as described above.

In another embodiment, storing the information includes storing the simulated output described above with the information for the single feature. For example, the simulated output that will be produced by the inspection system for the single feature may be stored with the design data coordinates for the single feature such that the information can be used together for the aligning and other steps described herein.

The method also includes aligning output of an inspection system for the wafer to the information for the single feature. Therefore, the single feature may be used as an to alignment mark for inspection. In addition, the stored information for the single feature may be referred to as an "alignment layer," which may be used during inspection or for inspection output alignment as described further herein. Aligning the output of the inspection system to the information for the single feature may be performed in a number of different ways. For example, the simulated output described above and the inspection system output can be aligned by pattern matching, image correlation, or any other suitable method and/or algorithm known in the art.

In one embodiment, the output that is aligned includes output in each of multiple swaths of output acquired by the inspection system for the wafer, and determining the position of the first portion as described further herein includes determining positions of each of first portions of the output in each of the multiple swaths aligned to the single feature in the design data space based on the position of the single feature in the design data space. Therefore, the embodiments described herein may be used for substantially high coordinate accuracy using swath alignment marks (the "single features" described herein) from design. As such, the embodiments described herein provide a way in which swaths can be aligned without critical design that is IP sensitive.

Each of the swaths may then be separately aligned to the design data space. For example, the information for the single feature may be aligned to the output in a first swath, then the output in a second swath, etc. Therefore, the same single feature may be used for alignment of each or more than one swath of inspection output. However, if different swaths of output are generated for different, mutually exclusive portions of the dies printed on the wafer, then all of the swaths may not contain output that can be aligned to the same single feature (e.g., if they do not all contain the same configuration of features that were merged into the one single feature). Therefore, the methods described herein may be performed to create more than one single feature, some of which are used for some swaths of output and others of which are used for other swaths of the output. The term "swath" as used herein is intended to have the meaning commonly assigned to that term in the art of wafer inspection. More than one feature may also be used to align a single swath since we may not get the best answer from a single site. Averaging many sites for a single swath reduces the chance of error.

Unlike the embodiments described herein, another way that swaths can be aligned without using an IP sensitive design is to use relatively large reticle marks on the wafer that are available for scanners and optical metrology tools. These marks are usually substantially large and do not contain any IP information. A few of these marks will be available along streets of the wafers. It is possible that the marks will be printed at a few locations on every swath. However, there is no guarantee that this will be the case. Therefore, the embodiments described herein that can guarantee the ability to align every swath are needed.

In some embodiments, aligning the output includes aligning the output of the inspection system for the wafer to the simulated output described herein for the single feature. For example, since the simulated output is generated to simulate the output that will be produced for the single feature by the inspection system, the simulated output may provide better alignment to the actual output than simply the periphery of the polygon defining the single feature. Such aligning may be performed as described further herein.

The method further includes determining a position of a first portion of the output aligned to the single feature in the design data space based on the position of the single feature in the design data space. Therefore, the embodiments generate a derivative of the design that removes all IP sensitive information from the design file and use it to align the design to inspection images. For example, once the single feature has been aligned to the output, the portion of the output that aligned to the single feature may be assigned the same design data coordinates as the single feature.

The method also includes determining positions in the design data space of other portions of the output based on the position of the first portion of the output in the design data space. For example, once the design data coordinates for at least a portion of a swath are determined as described above, those coordinates as well as the wafer space positions of the output relative to the aligned output may be used to propagate the design data space coordinates across the rest or at least another portion of the output in the swath. In this manner, the wafer output corresponding to the single feature may be aligned to the design and then other output can be aligned to the design data space based on its wafer space position relative to the aligned output.

The embodiments described herein have substantially high coordinate accuracy, which is substantially important for defect inspection tools, both in terms of the ability to accurately know the position of detected defects as well as to place targeted micro care areas that can eliminate nuisance detection from noisy regions adjoining the care areas. In addition, the embodiments described herein provide a way to improve coordinate accuracy without the need for IP sensitive design information. For example, the embodiments are able to substantially accurately place the inspection output in the design data space without, as described further above, compromising or exposing any IP sensitive design information. Therefore, the embodiments described herein allow device manufacturers and/or wafer inspectors to address a customer's IP concerns and at the same time be able to achieve the same or better coordinate accuracy than other currently available alignment techniques.

The embodiments described herein may or may not also include detecting defects on the wafer based on the output of the inspection system. Therefore, the output of the inspection system may be used for wafer inspection, and the wafer inspection may be performed before, during, or after the positions of the first and other portions of the output are determined in design data space. For example, the positions of the output in design data space may be determined and then defect detection may be performed. Alternatively, the defects may be detected on the wafer and then the positions of the output in the design data space may be determined for the first portions corresponding to the single feature alignment marks and then other portions corresponding to the defect locations. In this manner, determining the positions of the other portions of the output in the design data space may be performed for all of the output acquired by the inspection system for the wafer (e.g., entire swaths of output regardless of which individual output to in the entire swaths correspond to defects) or only for the output acquired by the inspection system that corresponds to the defects.

In another embodiment, the design data is not used by the inspection system during inspection of the wafer. The inspection that is performed using the output that has been aligned to design as described herein may include any inspection known in the art that can be performed in any manner. For example, the inspection may be context based inspection (CBI) or target based inspection (TBI), which have proven the value of coordinate accuracy beyond doubt. These inspections provide dramatic sensitivity improvements by improving coordinate accuracy and thereby care area placement accuracy. The embodiments described herein provide a general purpose ability to run all inspections with substantially high coordinate accuracy even when design is not available or cannot be used during the inspection due to IP concerns. Examples of CBI are described in U.S. Pat. No. 7,676,077 issued on Mar. 9, 2010 to Kulkarni et al., and examples of TBI are described in U.S. patent application Ser. No. 13/652,377 filed on Oct. 15, 2012 by Kenong Wu et al. This patent and this patent application are incorporated by reference as if fully set forth herein and the embodiments described herein may include any steps described therein and may be further configured as described therein. The embodiments described herein may therefore be configured for CBI or TBI without design.

One or more steps of the method may be performed by a computer system. For example, the merging step, the storing step, the aligning step, determining the position of the first portion, and determining the positions of the other portions are performed by one or more computer systems, which may be further configured as described herein. In some embodiments, the merging step and the storing step are performed with a first of the one or more computer systems, and the aligning step, determining the position of the first portion, and determining the positions of the other portions are performed with a second of the one or more computer systems. The first and second computer systems may be configured as described further herein.

Another embodiment relates to a method for determining a position of output of an inspection system in design data space. The method includes aligning output of an inspection system for a wafer to information for a single feature. More than one feature in design data for the wafer were merged into the single feature that has a periphery that encompasses all of the features that were merged. The information includes a position of the single feature in design data space. Therefore, the single feature and the information for the single feature may be created and stored by another method and/or system and used in this method.

The method also includes determining a position of a first portion of the output aligned to the single feature in the design data space based on the position of the single feature in the design data space. In addition, the method includes determining positions in the design data space of other portions of the output based on the position of the first portion of the output in the design data space. All of these steps may be further performed as described herein.

Aligning the output, determining the position of the first portion of the output, and determining the positions of the other portions are performed using a computer system, which may be configured as described herein. In one embodiment, the computer system is part of an inspection system, and the features were merged by a computer system of an electronic design automation (EDA) tool. These computer systems, the inspection system, and the EDA tool may be configured as described further herein.

Each of the embodiments of the methods described above may include any other step(s) of any other method(s) described herein. Furthermore, each of the embodiments of the methods described above may be performed by any of the systems described herein.

All of the methods described herein may include storing results of one or more steps of the method embodiments in a computer-readable storage medium. The results may include any of the results described herein and may be stored in any manner known in the art. The storage medium may include any storage medium described herein or any other suitable storage medium known in the art. After the results have been stored, the results can be accessed in the storage medium and used by any of the method or system embodiments described herein, formatted for display to a user, used by another software module, method, or system, etc.

Another embodiment relates to a non-transitory computer-readable medium storing program instructions for causing a computer system to perform a computer-implemented method for determining a position of output of an inspection system in design data space. One such embodiment is shown in FIG. 2. For example, as shown in FIG. 2, non-transitory computer-readable medium 200 stores program instructions 202 for causing computer system 204 to perform a computer-implemented method for determining a position of output of an inspection system in design data space. The computer-implemented method may include any step(s) of any method(s) described herein.

Program instructions 202 implementing methods such as those described herein may be stored on non-transitory computer-readable medium 200. The computer-readable medium may be a storage medium such as a magnetic or optical disk, or a magnetic tape or any other suitable non-transitory computer-readable medium known in the art.

The program instructions may be implemented in any of various ways, including procedure-based techniques, component-based techniques, andor object-oriented techniques, among others. For example, the program instructions may be implemented using Matlab, Visual Basic, ActiveX controls, C, C++ objects, C#, JavaBeans, Microsoft Foundation Classes ("MFC"), or other technologies or methodologies, as desired.

Computer system 204 may take various forms, including a personal computer system, mainframe computer system, workstation, system computer, image computer, programmable image computer, parallel processor, or any other device known in the art. In general, the term "computer system" may be broadly defined to encompass any device having one or more processors, which executes instructions from a memory medium.

An additional embodiment relates to a system configured to determine a position of output of an inspection system in design data space. The system includes a computer subsystem configured for merging more than one feature in design data for a wafer into a single feature that has a periphery that encompasses all of the features that are merged. The computer subsystem is also configured for storing information for the single feature without the design data for the features that are merged. The information includes a position of the single feature in design data space. The computer subsystem may be configured to perform these steps according to any of the embodiments described herein. This computer subsystem may also be configured to perform any other step(s) of any method(s) described herein.

In one embodiment, the computer subsystem is part of an EDA tool, and the inspection subsystem described further herein is not part of the EDA tool. For example, as shown in FIG. 3, the computer subsystem described above may be computer subsystem 300 included in EDA tool 302. The EDA tool and the computer subsystem included in such a tool may include any commercially available EDA tool that has been modified to perform the steps described herein. Therefore, the computer subsystem that is configured to perform the merging and storing steps described herein may be separate from an inspection subsystem of an inspection tool that is used to inspect the wafer. In other words, the design data containing critical IP information may be processed by one system or tool to create the alignment layer or information that will be used by another, different system or tool to perform alignment of inspection data or output. The computer subsystem that is used to create the alignment information also may not be part of an EDA tool and may be included in another system or tool or simply be configured as a stand alone computer system. Furthermore, although the alignment information may be generated by one tool and used by another tool, the tool or computer subsystem that generates the alignment information may be configured to provide that information to the to other tool by storing or transferring the alignment information to a shared computer-readable storage medium such as a fab database or by transmitting the alignment information directly to the tool that will use it, which may be performed as described further herein.

The system also includes an inspection subsystem configured for scanning the wafer to generate output for the wafer. One embodiment of such an inspection subsystem is shown in FIG. 3 as inspection subsystem 304. The inspection subsystem is configured to generate the output for a wafer by scanning the wafer with light and detecting light from the wafer during the scanning. For example, as shown in FIG. 3, the inspection subsystem includes light source 306, which may include any suitable light source known in the art.

Light from the light source may be directed to beam splitter 308, which may be configured to direct the light from the light source to wafer 310. The light source may be coupled to any other suitable elements (not shown) such as one or more condensing lenses, collimating lenses, relay lenses, objective lenses, apertures, spectral filters, polarizing components and the like. As shown in FIG. 3, the light may be directed to the wafer at a normal angle of incidence. However, the light may be directed to the wafer at any suitable angle of incidence including near normal and oblique incidence. In addition, the light or multiple light beams may be directed to the wafer at more than one angle of incidence sequentially or simultaneously. The inspection subsystem may be configured to scan the light over the wafer in any suitable manner.

Light from wafer 310 may be collected and detected by one or more channels of the inspection subsystem during scanning. For example, light reflected from wafer 310 at angles relatively close to normal (i.e., specularly reflected light when the incidence is normal) may pass through beam splitter 308 to lens 312. Lens 312 may include a refractive optical element as shown in FIG. 3. In addition, lens 312 may include one or more refractive optical elements and/or one or more reflective optical elements. Light to collected by lens 312 may be focused to detector 314. Detector 314 may include any suitable detector known in the art such as a charge coupled device (CCD) or another type of imaging detector. Detector 314 is configured to generate output that is responsive to the reflected light collected by lens 312. Therefore, lens 312 and detector 314 form one channel of the inspection subsystem. This channel of the inspection subsystem may include any other suitable optical components (not shown) known in the art.

Since the inspection subsystem shown in FIG. 3 is configured to detect light specularly reflected from the wafer, the inspection subsystem is configured as a BF inspection system. Such an inspection subsystem may, however, also be configured for other types of wafer inspection. For example, the inspection subsystem shown in FIG. 3 may also include one or more other channels (not shown). The other channel(s) may include any of the optical components described herein such as a lens and a detector, configured as a scattered light channel. The lens and the detector may be further configured as described herein. In this manner, the inspection subsystem may also be configured for DF inspection.

The inspection subsystem is configured for aligning the output for the wafer to the information for the single feature. The inspection subsystem is also configured for determining a position of a first portion of the output aligned to the single feature in the design data space based on the position of the single feature in the design data space. The inspection subsystem is further configured for determining positions in the design data space of other portions of the output based on the position of the first portion of the output in the design data space. These steps may be performed by the inspection subsystem as described further herein.

The inspection subsystem may also include a computer subsystem that is configured to perform these steps. For example, the optical elements described above may form optical subsystem 316 of inspection subsystem 304, which may also include computer subsystem 318 that is coupled to the optical subsystem. In this manner, output generated by the detector(s) during scanning may be provided to computer subsystem 318. For example, the computer subsystem may be coupled to detector 314 (e.g., by one or more transmission media shown by the dashed line in FIG. 3, which may include any suitable transmission media known in the art) such that the computer subsystem may receive the output generated by the detector.

The computer subsystem of the inspection subsystem may be configured to perform any step(s) described herein. For example, computer subsystem 318 may be configured for performing the aligning step, determining the position of the first portion, and determining the positions of the other portions as described herein. In addition, computer subsystem 318 may be configured to perform other steps described herein such as the merging and storing steps. Therefore, although some of the steps described herein may be performed by different computer subsystems, all of the steps of the method may be performed by a single computer subsystem such as that of the inspection subsystem or a stand alone computer system. In addition, the computer subsystem may be configured as a virtual inspector such as that described in U.S. Pat. No. 8,126,255 issued on Feb. 28, 2012 to Bhaskar et al., which is incorporated by reference as if fully set forth herein.

The computer subsystem of the inspection subsystem may also be coupled to the other computer subsystem that is not part of the inspection subsystem such as computer subsystem 300, which may be included in another tool such as the EDA tool described above such that computer subsystem 318 can receive output generated by computer subsystem 300, which may include the information for the single feature or any other alignment layer information generated by that computer subsystem. For example, the two computer subsystems may be effectively coupled by a shared computer-readable storage medium such as a fab database or may be coupled by a transmission medium such as that described above such that information may be transmitted between the two computer subsystems.

It is noted that FIG. 3 is provided herein to generally illustrate a configuration of an inspection subsystem that may be included in the system embodiments described herein. Obviously, the inspection subsystem configuration described herein may be altered to optimize the performance of the inspection subsystem as is normally performed when designing a commercial inspection system. In addition, the systems described herein may be implemented using an existing inspection subsystem (e.g., by adding functionality described herein to an existing inspection system) such as the 29xx/28xx series of tools that are commercially available from KLA-Tencor. For some such systems, the methods described herein may be provided as optional functionality of the system (e.g., in addition to other functionality of the system). Alternatively, the system described herein may be designed "from scratch" to provide a completely new system.

Further modifications and alternative embodiments of various aspects of the invention will be apparent to those skilled in the art in view of this description. For example, systems and methods for determining a position of inspection system output in design data space are provided. Accordingly, this description is to be construed as illustrative only and for the purpose of teaching those skilled in the art the general manner of carrying out the invention. It is to be understood that the forms of the invention shown and described herein are to be taken as the presently preferred embodiments. Elements and materials may be substituted for those illustrated and described herein, parts and processes may be reversed, and certain features of the invention may be utilized independently, all as would be apparent to one skilled in the art after having the benefit of this description of the invention. Changes may be made in the elements described herein without departing from the spirit and scope of the invention as described in the following claims.

What is claimed is:

1. A method for determining a position of output of an inspection system in a design data space, comprising:
   merging more than one feature in design data for a wafer into a single feature that has a periphery that encompasses all of the features that are merged;
   storing information for the single feature without the design data for the features that are merged, wherein the information comprises a position of the single feature in a design data space;
   aligning output of an inspection system for the wafer to the information for the single feature;
   determining a position of a first portion of the output aligned to the single feature in the design data space based on the position of the single feature in the design data space; and
   determining positions in the design data space of other portions of the output based on the position of the first portion of the output in the design data space, wherein the merging step, the storing step, the aligning step, determining the position of the first portion, and determining the positions of the other portions are performed by one or more computer systems.

2. The method of claim 1, wherein the output that is aligned comprises output in each of multiple swaths of output acquired by the inspection system for the wafer, and wherein determining the position of the first portion comprises determining positions of each of first portions of the output in each of the multiple swaths aligned to the single feature in the design data space based on the position of the single feature in the design data space.

3. The method of claim 1, wherein the single feature comprises a bounding polygon defining the periphery of the single feature, wherein the single feature comprises no additional features within the periphery, and wherein the bounding polygon contains no additional polygons.

4. The method of claim 1, wherein said merging eliminates any intellectual property in the design data from the information for the single feature.

5. The method of claim 1, wherein storing the information comprises storing the information in a storage medium in which the design data is not stored.

6. The method of claim 1, wherein the features that are merged have at least one lateral dimension on the wafer that is less than 100 nm, and wherein the inspection system is not capable of resolving features printed on the wafer having a lateral dimension that is less than 200 nm.

7. The method of claim 1, further comprising identifying isolated features in the design data, wherein the information that is stored does not include the design data for the isolated features.

8. The method of claim 1, wherein the features that are merged comprise dense features in the design data.

9. The method of claim 1, wherein the features that are merged comprise features in a random logic area of the design data.

10. The method of claim 1, wherein said merging comprises merging two or more sets of more than one feature in the design data into corresponding single features, wherein said storing comprises storing information for the corresponding single features without the design data for the features that are merged, and wherein the method further comprises selecting the single feature whose information will be used in the aligning step by acquiring output of the inspection system at locations of the corresponding single features on the wafer and selecting one of the corresponding single features that will provide more accurate alignment than others of the corresponding single features.

11. The method of claim 1, further comprising simulating output that will be produced for the single feature by the inspection system based on the information for the single feature, wherein said storing comprises storing the simulated output with the information for the single feature.

12. The method of claim 11, wherein said aligning comprises aligning the output of the inspection system for the wafer to the simulated output for the single feature.

13. The method of claim 1, wherein said merging comprises merging two or more sets of more than one feature in the design data into corresponding single features, and wherein the method further comprises selecting the single feature whose information will he used in the aligning step from the corresponding single features.

14. The method of claim 1, wherein the design data is not used by the inspection system during inspection of the wafer.

15. The method of claim 1, wherein the inspection system is configured as a bright field inspection system.

16. The method of claim 1, wherein the merging step and the storing step are performed with a first of the one or more computer systems, and wherein the aligning step, determining the position of the first portion, and determining the positions of the other portions are performed with a second of the one or more computer systems.

17. A method for determining a position of output of an inspection system in a design data space, comprising:
  aligning output of an inspection system for a wafer to information for a single feature, wherein more than one feature in design data for the wafer were merged into the single feature that has a periphery that encompasses all of the features that were merged, and wherein the information comprises a position of the single feature in a design data space;
  determining a position of a first portion of the output aligned to the single feature in the design data space based on the position of the single feature in the design data space; and
  determining positions in the design data space of other portions of the output based on the position of the first portion of the output in the design data space, wherein aligning the output, determining the position of the first portion, and determining the positions of the other portions are performed using a computer system.

18. The method of claim 17, wherein the computer system is part of an inspection system, and wherein the features were merged by a computer system of an electronic design automation tool.

19. A system configured to determine a position of output of an inspection system in a design data space, comprising:
  a computer subsystem configured for:
    merging more than one feature in design data for a wafer into a single feature that has a periphery that encompasses all of the features that are merged; and
    storing information for the single feature without the design data for the features that are merged, wherein the information comprises a position of the single feature in a design data space; and
  an inspection subsystem configured for:
    scanning the wafer to generate an output for the wafer;
    aligning the output for the wafer to the information for the single feature;
    determining a position of a first portion of the output aligned to the single feature in the design data space based on the position of the single feature in the design data space; and
    determining positions in the design data space of other portions of the output based on the position of the first portion of the output in the design data space.

20. The system of claim 19, wherein the computer subsystem is part of an electronic design automation tool, and wherein the inspection subsystem is not part of the electronic design automation tool.

21. The system of claim 19, wherein the output that is aligned comprises output in each of multiple swaths of output acquired by the inspection subsystem for the wafer, and wherein determining the position of the first portion comprises determining positions of each of first portions of the output in each of the multiple swaths aligned to the single feature in the design data space based on the position of the single feature in the design data space.

22. The system of claim 19, wherein the single feature comprises a bounding polygon defining the periphery of the single feature, wherein the single feature comprises no additional features within the periphery, and wherein the bounding polygon contains no additional polygons.

23. The system of claim 19, wherein said merging eliminates any intellectual property in the design data from the information for the single feature.

24. The system of claim 19, wherein storing the information comprises storing the information in a storage medium in which the design data is not stored.

25. The system of claim 19, wherein the features that are merged have at least one lateral dimension on the wafer that is less than 100 nm, and wherein the inspection subsystem is not capable of resolving features printed on the wafer having a lateral dimension that is less than 200 nm.

26. The system of claim 19, wherein the computer subsystem is further configured for identifying isolated features in the design data, and wherein the information that is stored does not include the design data for the isolated features.

27. The system of claim 19, wherein the features that are merged comprise dense features in the design data.

28. The system of claim 19, wherein the features that are merged comprise features in a random logic area of the design data.

29. The system of claim 19, wherein said merging comprises merging two or more sets of more than one feature in the design data into corresponding single features, wherein said storing comprises storing information for the corresponding single features without the design data for the features that are merged, and wherein the computer subsystem is further configured for selecting the single feature whose information will be used in the aligning step by acquiring output of the inspection subsystem at locations of the corresponding single features on the wafer and selecting one of the corresponding single features that will provide more accurate alignment than others of the corresponding single features.

30. The system of claim 19, wherein the computer subsystem is further configured for simulating output that will be produced for the single feature by the inspection subsystem based on the information for the single feature, and wherein said storing comprises storing the simulated output with the information for the single feature.

31. The system of claim 30, wherein said aligning comprises aligning the output of the inspection subsystem for the wafer to the simulated output for the single feature.

32. The system of claim 19, wherein said merging comprises merging two or more sets of more than one feature in the design data into corresponding single features, and wherein the computer subsystem is further configured for selecting the single feature whose information will be used in the aligning step from the corresponding single features.

33. The system of claim 19, wherein the design data is not used by the inspection subsystem during inspection of the wafer.

34. The system of claim 19, wherein the inspection subsystem is configured as a bright field inspection subsystem.

* * * * *